(12) United States Patent (10) Patent No.: US 12,653,219 B2
Komorowski (45) Date of Patent: Jun. 16, 2026

(54) METHODS OF PRODUCTION OF ARGININE-SILICATE COMPLEXES

(71) Applicant: Nutrition21, LLC, Saddle Brook, NJ (US)

(72) Inventor: James R. Komorowski, Trumbull, CT (US)

(73) Assignee: Nutrition21, LLC, Saddle Brook, NJ (US)

( * ) Notice: Subject to any disclaimer, the term of this patent is extended or adjusted under 35 U.S.C. 154(b) by 371 days.

(21) Appl. No.: 18/192,023

(22) Filed: Mar. 29, 2023

(65) Prior Publication Data

US 2023/0225387 A1 Jul. 20, 2023

Related U.S. Application Data

(63) Continuation of application No. 17/390,723, filed on Jul. 30, 2021, now Pat. No. 11,622,571, which is a continuation of application No. 17/150,892, filed on Jan. 15, 2021, now Pat. No. 11,103,000, which is a continuation of application No. 17/124,361, filed on Dec. 16, 2020, now abandoned.

(Continued)

(51) Int. Cl.
| | |
|---|---|
| *A23L 33/175* | (2016.01) |
| *A23B 2/93* | (2025.01) |
| *A23L 2/52* | (2006.01) |
| *A23L 33/165* | (2016.01) |
| *C07C 277/08* | (2006.01) |
| *C07C 279/14* | (2006.01) |

(52) U.S. Cl.
CPC .............. *A23L 33/175* (2016.08); *A23B 2/93* (2025.01); *A23L 2/52* (2013.01); *C07C 277/08* (2013.01); *C07C 279/14* (2013.01); *A23V 2002/00* (2013.01)

(58) Field of Classification Search
CPC .. A61K 47/26; A61K 2800/412; A61K 31/70; A61K 31/695; A23L 33/175; A23L 33/165; A23L 27/00; A23L 2/52; A23L 3/46; C07C 277/08; C07C 279/14; C07C 211/14
USPC ......... 426/590, 489, 74, 648, 464, 471, 473, 426/654; 556/9; 514/23, 63
See application file for complete search history.

(56) References Cited

U.S. PATENT DOCUMENTS

| | | | |
|---|---|---|---|
| 1,980,589 A | 11/1934 | Acree | |
| 3,249,441 A | 5/1966 | Reynolds et al. | |

(Continued)

FOREIGN PATENT DOCUMENTS

| | | | |
|---|---|---|---|
| CN | 106689696 A | 5/2017 | |
| DE | 20315174 U1 | 12/2003 | |

(Continued)

OTHER PUBLICATIONS

Anonymous, "Bonded arginine silicate: raising the bar", Nutraceutical Business Review (2015).

(Continued)

*Primary Examiner* — Hong T Yoo
(74) *Attorney, Agent, or Firm* — Foley Hoag LLP; Lucas P. Watkins; Benjamin A. Vaughan

(57) ABSTRACT

Methods of manufacturing inositol-stabilized arginine-silicate ("ASI") complexes with reduced or eliminated clumping and with increased solubility.

20 Claims, 6 Drawing Sheets

Related U.S. Application Data

(60) Provisional application No. 62/948,591, filed on Dec. 16, 2019.

(56) References Cited

U.S. PATENT DOCUMENTS

| | | | |
|---|---|---|---|
| 3,337,403 | A | 8/1967 | Zentner |
| 4,297,349 | A | 10/1981 | Barcza |
| 4,385,052 | A | 5/1983 | Zackheim et al. |
| 4,573,996 | A | 3/1986 | Kwiatek et al. |
| 4,597,961 | A | 7/1986 | Etscorn |
| 4,839,174 | A | 6/1989 | Baker et al. |
| 4,847,082 | A | 7/1989 | Sabin |
| 4,908,213 | A | 3/1990 | Govil et al. |
| 4,943,435 | A | 7/1990 | Baker et al. |
| 5,166,168 | A | 11/1992 | Stiefel |
| 5,217,997 | A | 6/1993 | Levere et al. |
| 5,250,569 | A | 10/1993 | Godfrey |
| 5,284,657 | A | 2/1994 | Lu et al. |
| 5,288,497 | A | 2/1994 | Stanley et al. |
| 5,622,980 | A | 4/1997 | Caldwell et al. |
| 5,656,264 | A | 8/1997 | Hanada et al. |
| 5,662,920 | A | 9/1997 | Santus |
| 5,707,970 | A | 1/1998 | McCarty et al. |
| 5,716,610 | A | 2/1998 | Jack et al. |
| 5,763,392 | A | 6/1998 | Hansen et al. |
| 5,763,496 | A | 6/1998 | Holland |
| 5,804,203 | A | 9/1998 | Hahn et al. |
| 6,066,659 | A | 5/2000 | Speck |
| 6,123,936 | A | 9/2000 | Platz et al. |
| 6,132,394 | A | 10/2000 | Lankinen |
| 6,156,735 | A | 12/2000 | McCarty et al. |
| 6,182,655 | B1 | 2/2001 | Keller et al. |
| 6,298,847 | B1 | 10/2001 | Datta et al. |
| 6,344,444 | B1 | 2/2002 | McCarty et al. |
| 6,387,394 | B1 | 5/2002 | Baichwal et al. |
| 6,418,926 | B1 | 7/2002 | Chawla |
| 6,462,051 | B1 | 10/2002 | Nozawa et al. |
| 6,803,456 | B1 | 10/2004 | Kuhlmann |
| 7,576,132 | B2 | 8/2009 | Juturu et al. |
| 7,972,633 | B2 | 7/2011 | Smith |
| 8,524,279 | B2 | 9/2013 | Snyder et al. |
| 9,339,467 | B2 | 5/2016 | Beyerinnck et al. |
| 10,959,971 | B2 | 3/2021 | Komorowski |
| 11,103,000 | B2 | 8/2021 | Komorowski |
| 11,191,735 | B2 | 12/2021 | Komorowski et al. |
| 11,622,571 | B2 | 4/2023 | Komorowski |
| 2002/0068365 | A1 | 6/2002 | Kuhrts |
| 2003/0028169 | A1 | 2/2003 | Fossel |
| 2004/0009746 | A1 | 1/2004 | Korman |
| 2004/0097467 | A1 | 5/2004 | Juturu et al. |
| 2004/0204387 | A1 | 10/2004 | McLaurin |
| 2006/0204455 | A1 | 9/2006 | Giniger |
| 2007/0020206 | A1 | 1/2007 | Jermann et al. |
| 2007/0116831 | A1 | 5/2007 | Prakash et al. |
| 2010/0062102 | A1 | 3/2010 | Knap et al. |
| 2010/0291195 | A1 | 11/2010 | Fossel |
| 2012/0064126 | A1 | 3/2012 | Sung et al. |
| 2012/0141588 | A1 | 6/2012 | Chopra et al. |
| 2013/0034530 | A1 | 2/2013 | Fantz |
| 2013/0101569 | A1 | 4/2013 | Weston |
| 2013/0142905 | A1 | 6/2013 | Gibbons et al. |
| 2013/0216586 | A1 | 8/2013 | LeBrun et al. |
| 2016/0081959 | A1 | 3/2016 | Bartos et al. |
| 2016/0263135 | A1 | 9/2016 | Komorowski et al. |
| 2016/0297722 | A1* | 10/2016 | Littmann .............. C07C 215/50 |
| 2017/0000809 | A1 | 1/2017 | Komorowski |
| 2017/0135969 | A1 | 5/2017 | Komorowski |
| 2017/0348235 | A1 | 12/2017 | White |
| 2019/0000126 | A1* | 1/2019 | Hesse .................. A23L 33/125 |
| 2020/0138761 | A1 | 5/2020 | Komorowski |
| 2021/0127713 | A1 | 5/2021 | Miranda et al. |
| 2021/0177029 | A1 | 6/2021 | Komorowski |
| 2021/0205251 | A1 | 7/2021 | Komorowski |
| 2021/0352947 | A1 | 11/2021 | Komorowski |
| 2023/0100521 | A1 | 3/2023 | Komorowski |
| 2023/0225387 | A1 | 7/2023 | Komorowski |
| 2023/0363417 | A1 | 11/2023 | Guo et al. |
| 2025/0024860 | A1 | 1/2025 | Hammock et al. |

FOREIGN PATENT DOCUMENTS

| | | | |
|---|---|---|---|
| EP | 1040815 A1 | 10/2000 | |
| EP | 1911357 A1 | 4/2008 | |
| EP | 2805730 A1 | 11/2014 | |
| FR | 2610522 A1 | 8/1988 | |
| FR | 2745498 A1 | 9/1997 | |
| JP | S60094949 A | 5/1985 | |
| JP | S6125688 B2 | 6/1986 | |
| JP | S62207209 A | 9/1987 | |
| JP | H04 169528 A | 6/1992 | |
| JP | 2001181211 A | 7/2001 | |
| JP | 2006501224 A | 1/2006 | |
| JP | 2007503407 A | 2/2007 | |
| JP | 200754041 A | 3/2007 | |
| JP | 2013529623 A | 7/2013 | |
| JP | 2015522630 A | 8/2015 | |
| JP | 2018529769 A | 10/2018 | |
| KR | 1020000070977 A | 11/2000 | |
| WO | WO-96/16633 A1 | 6/1996 | |
| WO | WO-1998/34647 A1 | 8/1998 | |
| WO | WO-2000/45651 A1 | 8/2000 | |
| WO | WO-2002/28379 A2 | 4/2002 | |
| WO | WO-2004/017913 A2 | 3/2004 | |
| WO | WO-2007/13655 A1 | 2/2007 | |
| WO | WO-2011/161421 A1 | 12/2011 | |
| WO | WO-2012/119007 A1 | 9/2012 | |
| WO | WO-2012/173808 A1 | 12/2012 | |
| WO | WO-2014/016003 A1 | 1/2014 | |
| WO | WO-2016112170 A1 * | 7/2016 | ............ A23L 33/115 |
| WO | WO-2017/004226 A1 | 1/2017 | |
| WO | WO-2018/089516 A1 | 5/2018 | |
| WO | WO-2020/058226 A1 | 3/2020 | |
| WO | WO-2020/092431 A1 | 5/2020 | |
| WO | WO-2021/127048 A1 | 6/2021 | |
| WO | WO-2023/086567 A1 | 5/2023 | |

OTHER PUBLICATIONS

Komorowski et al., "Arginine silicate supplementation decreases markers of cardiovascular, renal and metabolic dysfunction and increases markers of vasodilation and cardiovascular health in healthy adult males", The FASEB Journal 29: 748-2 (2015).

Abstracts taken from "Drying an overview", pp. 1-7. Dyveikov et al., "Advances in Spray-Drying Processes" 2014, and Kumar "Status and Future Prospects of Fructooligosaccharides as Nutraceuticals", 2018, www.sciencedirect.com/topics/agricultural-andbiological/sciences/sprav-drvina. (Year: 2014).

Al-Qazzaz et al.; "Cognitive impairment and memory dysfunction after a stroke diagnosis: a post-stroke memory assessment," Neuropsychiatric Disease and Treatment 10: pp. 1677-1691 (2014).

Allen et al. Ansel's Pharmaceutical Dosage Forms and Drug Delivery Systems, 8th Edition, eds., Lippincott Williams & Wilkins, Philadelphia, PA, 2005.

Asai et al., "Topical application of ex vivo expanded endothelial progenitor cells promotes vascularization and wound healing in diabetic mice," International Wound Journal pp. 527-533 (2012).

Ask the dentist, how often should I go to the dentist for a teeth cleaning? [online], [retrieved Jul. 21, 2018]. Retrieved from the Internet: <URL: https://askthedentist.com/how-often-should-i-go-to-the-dentist-for-a-teeth-cleaning/>.

Barak et al., "Inositol Treatment of Alzheimer's Disease: A Double Blind, Cross-over Placebo Controlled Trial," Progress in Neuro-Psychopharmacology and Biological Psychiatry 20: pp. 729-735 (1996).

Bassler, "Hard water, food fibre, and silicon," British Medical Journal 1: pp. 919 (1978).

Bonnefont-Rousselot, "Glucose and reactive oxygen species," Curr. Opin. Clin. Nutr. Metab. Care 5: pp. 561-568 (2002).

Calles-Escandon et al., "Diabetes and endothelial dysfunction: A clinical perspective," Endocrine Reviews 22(1): pp. 36-52 (2001).

(56)　　　　　References Cited

OTHER PUBLICATIONS

Calver et al., "Effect of local intra-arterial NG-monomethyl-L-arginine in patients with hypertension: the nitric oxide dilator mechanism appears abnormal," J. of Hypertension 10: pp. 1025-1031 (1992).

Carlisle et al., "A silicon requirement for normal growth of cartilage in culture," Fed. Proc. 39: pp. 787 (1980).

Carlisle, "Silicon: An Essential Element for the Chick," Science 178: pp. 619-621 (1972).

Carlisle. "Biochemical and morphological change associated with long bone abnormalities in silicon deficiency". J. Nutr. 110: pp. 1046-1055 (1980).

Carlisle. "In vivo Requirement for Silicon in Articular Cartilage and Connective Tissue Formation in the Chick," J. Nutr. 106(4): pp. 78-484 (1976).

Carlson et al., "Predictors of neurocognitive outcomes on antiretroviral therapy after cryptococcal meningitis: a prospective cohort study," Metabolic Brian Disease 29(2): pp. 269-279 (2014).

Chen et al., "L-Arginine Abrogates Salt-sensitive Hypertension in Dahl/Rapp Rats," J. Clin. Invest. 88: pp. 1559-1567 (1991).

Cherian et al., "L-arginine and Free Radical Scavengers Increase Cerebral Blood Flow and Brain Tissue Nitric Oxide Concentrations after Controlled Cortical Impact Injury in Rats," J. of Neurotrauma 20(1): pp. 77-85 (2003).

Chronic Fatigue and Immune Dysfunction Syndrome (CFIDS): Alternative Approaches, DoctorYourself.com [online], [retrieved on Nov. 27, 2017]. Retrieved from the Internet: <URL: <http://www.doctoryourself.com/fatigue.html>, 2005.

Clarkson et al., "Oral L-Arginine Improves Endothelium-dependent Dilation in Hypercholesterolemic Young Adults," J. Clin. Invest. 97(8): pp. 1989-1994 (1996).

Clowes et al., "Suppression by heparin of smooth muscle cell proliferation in injured arteries," Nature 265: pp. 625-626 (1977).

Cooke et al., "Is NO an Endogenous Antiatherogenic Molecule," Arteriosclerosis and Thrombosis 14(5): pp. 653-655 (1994).

Cosgrove, "Nitric Oxide Ingredients for Sports," Nutritional Outlook, [online], Nov. 8, 2013. Retrieved from the Internet: <URL: http://www.nutritionaloutlook.com/heart-health/nitricoxide-ingredients-sports>.

Creager et al., "L-Arginine Improves Endothelium-dependent Vasodilation in Hypercholesterolemic," Humans J. Clin. Invest. 90: pp. 1248-1253 (1992).

Curtis et al., "Nitric oxide supplementation of synthesis of block-which is the better approach to treatment of heart disease?", Trends in Pharmacological Sciences, 18(7): pp. 239-244 (1997).

Drexler et al., "Correction of endothelial dysfunction in coronary microcirculation of hypercholesterolaemic patients by L-arginine," Lancet 338: pp. 1546-1550 (1991).

Edelman et al., "Effect of controlled adventitial heparin delivery on smooth muscle cell proliferation following endothelial injury," Proc. Natl. Acad. Sci. USA 87: pp. 3773-3777 (1990).

Edmonds et al., "Water consumption, not expectancies about water consumption, affects cognitive performance in adults," Appetite 60: pp. 148-153 (2013).

Eisinger et al., "Effects of silicon, fluoride, etidronate and magnesium on bone mineral density: a retrospective study," Magnisium Research 6(3): pp. 247-249 (1993).

Extended European Search Report for EP Application No. 19878282.3 dated Jul. 26, 2022.

Garson et al., "Organosilicon Entities as Prophylactic and Therapeutic Agents," J. of Pharmaceutical Sciences 60(8): pp. 1113-1127 (1971).

Geoffrey Stark, DDS, "How much toothpaste per brushing is recommended?" [online], [retrieved Jul. 23, 2018]. Retrieved from the Internet: <URL: https ://secure.advantagedental.com/i mages/fi les/faq_toothpaste. htm>.

Goodman and Gilman's: The Pharmacological Basis of Therapeutics, 8th Ed., Gilman et al., eds., Pergamon Press, Elmsford, NY, 1990.

Greenhalgh et al., "PDGF and FGF stimulate wound healing in the genetically diabetic mouse," American Journal of Pathology 136(6): pp. 1235-1246 (1990).

Guyton et al., "Inhibition of rat arterial smooth muscle cell proliferation by heparin," Gire. Res. 46: pp. 625-634 (1980).

Harrison's Principles of Internal Medicine, 13.sup.th edition, vol. 2, Isselbacher et al. (eds.), published 1994 by McGraw-Hill in 1994, pp. 1321.

Hoogman et al., "Cognitive outcome in adults after bacterial meningitis," Journal of Neurology, Neurosurgery & Psychiatry 78(10): pp. 1092-1096 (2007).

Hott et al., "Short-term effects of organic silicon on trabecular bone in mature ovariectomized rats," Calcif. Tissue Int. 53: pp. 174-179 (1993).

Hung et al., "Cognitive Decline among Patients with Chronic Obstructive Pulmonary Disease," American Journal of Respiratory and Critical Care Medicine 180(2): pp. 134-137 (2009).

Im-Emsap et al., Chapter 9: Disperse Systems, in Modern Pharmaceutics, 4th Edition, Banker et al., eds., Marcel Dekker, Inc., New York NY, pp. 237-285 (2002).

International Search Report and Written Opinion for Application No. PCT/US16/040128 dated Aug. 26, 2016.

International Search Report and Written Opinion for Application No. PCT/US19/58653 dated Jan. 27, 2020.

International Search Report and Written Opinion for Application No. PCT/US20/65418 dated Mar. 8, 2021.

International Search Report and Written Opinion for Application No. PCT/US2022/049703 dated Apr. 13, 2023.

Kalman et al., "A clinical evaluation to determine the safety, pharmacokinetics, and pharmacodynamics of an inositol-stabilized arginine silicate dietary supplement in healthy adult males," Clinical Pharmacology: Advances and Applications 7: pp. 103-109 (2015).

Kalman et al., "Randomized prospective double-blind studies to evaluate the cognitive effects of inositol-stabilized arginine silicate in healthy physically active adults" Nutrients, 8(11): 736 (2016).

Kelly et al., "Insulin resistance: lifestyle and nutritional interventions," Alternative Medicine Review 5(2): pp. 109-132 (2000).

Kelly et al., "L-Theanine and Caffeine in Combination Affect Human Cognition as Evidenced by Oscillatory alpha-Band Activity and Attention Task Performance," J. Nutr. 138(8): pp. 1572S-1577S (2008).

Kirkorian et al., "Improved cognitive-cerebral function in older adults with chromium supplementation," Nutritional Neuroscience 13(3): pp. 116-122 (2010).

Kottke et al., Chapter 10: Tablet Dosage Forms, in Modern Pharmaceutics, 4th Edition, Banker et al., eds., Marcel Dekker, Inc., New York NY pp. 287-333 (2002).

Kumar et al., "Promising Therapeutics with Natural Bioactive Compounds for Improved Learning and Memory—A Review of Randomized Trials," Molecules 17: pp. 10503-10539 (2012).

Kurmann et al.; "Progressive multifocal leukoencephalopathy in common variable immunodeficiency: mitigated course under mirtazapine and mefloquine," Journal of Neurovirology 21(6): pp. 694-701 (2015).

Laurant et al., "Dietary L-Arginine Attenuates Blood Pressure in Mineralocorticoid-Salt Hypertensive Rats," Clin. and Exper. Hypertension 17(7): pp. 1009-1024 (1995).

Lieberman et al., Pharmaceutical Dosage Forms: Tablets, eds., Marcel Dekker, Inc., New York, NY, 1989.

Lockhart et al., "Cognition enhancing or neuroprotective compounds for the treatment of cognitive disorders: why? when? which?" Experimental Gerontology 38: pp. 1119-1128 (2003).

Loeper et al., "The Antiatheromatous Action of Silicon," Atherosclerosis 33: pp. 397-408 (1979).

Loeper et al., "The Physiological Role of the Silicon and its Antiatheromatous Action," in Biochemistry of Silicon and Related Problems, Bendz G et al. Eds . . . Plenum Press, NY, 1978; nn. 281-296.

Luscher., "Endothelium-derived nitric oxide: The endogenous nitrovasodilator in the human cardiovascular system," Eur. Heart J. 12(Suppl. E): pp. 2-11 (1991).

(56) References Cited

OTHER PUBLICATIONS

Marsh et al., "Relationships Among Balance, Visual Search, and Lacrosse-Shot Accuracy," J Strength Cond Res 24(6): pp. 1507-1514 (2010).

Maulik et al., "Nitric Oxide signaling in ischemic heart," Cardiovasc. Res. 30(4): pp. 593-601 (1995).

McPherson et al., "Superoxide activates constitutive nitric oxide synthase in a brain particulate fraction," Biochemical and Biophysical Research Communications 296: pp. 413-418 (2002).

Miller et al., "Practical Clinical Application of Biochemical Markers of Bone Turnover," Journal of Clinical Densitometry 2(3): pp. 323-342 (1999).

Mind Lab Pro®, "Nootropics for Gamers—Level Up Your Gaming With Cognitive Enhancers," Nootropics for Gamers—Level Up Your Gaming with Cognitive Enhancers, 2018, [onlinel][retrieved on Dec. 18, 2019]. Retrieved from the Internet: <URL: https://www.mindlabpro.com/blogs/nootropics/nootropics-gamers-gaming>.

Moncada et al., "The L-Arginine-Nitric Oxxide Pathway," The New. Engl. J. of Med. 329(27): pp. 2002-2012 (1993).

Nitric Oxide Benefits, Supplements, Sources, and Side Effects, [online], [dated May 24, 2015]. Retrieved from the Internet: <URL: https://web.archive.org/web/20150524100645/http://www.nitricoxide.org: 801>.

Nitrosigine Launch, [online], [dated May 16, 2013]. Retrieved from the Internet: <URL: https://nutrition21.com/nutrition-21-launches-nitrosigine-a-novel-patented-source-of-inositol-stabilized-arginine-silicate-accepted-by-the-fda-as-a-new-dietary-ingredient/>.

Nutrition 21, Inc., EurekAlert!, [online], public release Dec. 13, 2007. Retrieved from the Internet: <URL: https://www.eurekalert.org/pub releases/2007-12/n2-ncd121207.php>.

Parr, "Silicon, Wine, and the Heart," Lancet pp. 1087 (1980).

Partial European Search Report for European Application No. 03793307.4, dated Aug. 2, 2007.

Proctor et al., "A novel complex of arginine-silicate improved micro and macrovascular function and inhibits glomerular sclerosis in insulin-resistant JCR:LA-cp rats," Diabetologia 48(9): pp. 1925-1932 (2005).

Proctor et al., "Metabolic effects of a novel silicate inositol complex of the nitric oxide precursor arginine in the obese insulin-resistant JCR:LA-cp rat," Metabolism Clinical and Experimental 56: pp. 1318-1325 (2007).

Rood-Ojalvo et al., "The benefits of inositol-stabilized arginine silicate as a workout Ingredient," Journal of the International Society of Sports Nutrition 12(Suppl 1): pp. 14 (2015).

Rubanyi, "Endothelium-Derived Vasoactive Factors in Health and Disease," in Cardiovascular Significance of Endothelium-Derived Vasoactive Factors, Rubanyi, G.M., ed., Futura Publishina Company, Inc., NY xi-xix, 1991.

Sahin et al., "Effects of dietary supplementation of arginine-silicate-inositol complex on absorption and metabolism of calcium of laying hens", PloS one 13(1): pp. 1-12 (2018).

Salt metathesis reaction, Wikipedia [online], [retrieved 2018]. Retrieved from the Internet: <URL: https://en.wikipedia.ora/wiki/Salt metathesis reaction>.

Schiffman et al., "Taste of nutrients: amino acids, vitamins and fatty acids," Perception & Physcophisics 17(2): pp. 140-146 (1975).

Schwarz et al., "Growth-promoting Effects of Silicon in Rats," Nature 239: pp. 333-334 (1972).

Schwarz et al., "Inverse Relation of Silicon in Drinking Water and Atherosclerosis in Finland," Lancet pp. 538-539 (1977).

Schwarz, "Significance and Functions of Silicon in Warm-Blooded Animals," in Biochemistry of Silicon and Related Problems, Bendz, G et al., Eds., Plenum Press, NY, pp. 207-230 (1978).

Schwarz, "Silicon, Fibre, and Atherosclerosis," Lancet pp. 454-457 (1977).

Sowinski et al., "Effects of inositol-enhanced bonded arginine silicate ingestion on cognitive and executive function in gamers," Nutrients 13(11): pp. 3758 (2021).

Supplementary European Search Report for European Application No. EP 03793307.4 dated Dec. 4, 2008.

Svehla. "Reaction of Silicates," Vogels Textbook of Macro and Semimicro Qualitative Inorganic Analysis 5th Edition, Longman, London, pp. 350-353 (1979).

Tartar et al., "A prospective study evaluating the effects of a nutritional supplement intervention on cognition, mood states, and mental performance in video gamers", Nutrients 11(10): pp. 2326 (2019).

Toker et al., "The effects of hydrogen sulphide on alveolar bone loss in periodontitis," Minerva Stomatol 63(4): pp. 103-110 (2014).

Tsao et al., "Enhanced endothelial adhesiveness in hypercholesterolemia is attenuated by L-arginine," Circulation 89(5): pp. 2176-2182 (1994).

Van Lente, "Markers of inflammation as predictors in cardiovascular disease," Clinica Chimica Acta. 293: pp. 31-52 (2000).

Vitamin B8 (Inositol) Benefits for Brain Power, *Nootriment*, retrieved from <https://nootriment.com/vitamin-b8/> on Oct. 14, 2022, published Apr. 16, 2018.

Wang et al. "Effects of nitric oxide synthase inhibitors on systemic hypotension, cytokines and inducible nitric oxide synthase expression and lung injury following indotoxin administration in rats," J. Biomed. Sci. 6: pp. 28-35 (1999).

Wilson et al., "Impaired cognitive function and mental performance in mild dehydration," European Journal of Clinical Nutrition 57(2): pp. S24-S29 (2003).

Zempleni et al., "Biotin biochemistry and human requirements," J. Nutr. Biochem. 10: pp. 128-138 (1999).

CDC, "Long COVID or Post-COVID Conditions," retrieved from <www.cdc.gov/coronavirus/2019-ncov/long-term-effects/index.html> on Dec. 12, 2023, pp. 1-4.

Dickinson et al., "Bacterial Meningitis in children and adolescence: an observational study based on the national surveillance system," 2005, BMC Infectious Diseases, vol. 5, No. 103, pp. 1-17.

Dyveikov et al., "Chapter 6—New Advances in Spray-Drying Processes", Microencapsulation in the Food Industry, ; Academic Press, Abstract, (2014).

International Search Report and Written Opinion for International Application No. PCT/US21/46998 dated Jan. 21, 2022.

Kumar et al., "Chapter 14—Status and Future Prospects of Fructooligosaccharides as Nutraceuticals", Role of Materials Science in Food Bioengineering, Academic Press, Abstract, (2018).

Tugnait et al., "Gingival recession—its significance and management," Journal of Dentistry 29.6 (2001): 381-394.

\* cited by examiner

METHODS OF PRODUCTION OF ARGININE-SILICATE COMPLEXES

INCORPORATION BY REFERENCE TO RELATED APPLICATIONS

This application is a continuation of U.S. application Ser. No. 17/390,723, now U.S. Pat. No. 11,622,571 filed Jul. 30, 2021, which is a continuation of U.S. application Ser. No. 17/150,892, now U.S. Pat. No. 11,103,000 filed Jan. 15, 2021, which is a continuation of U.S. application Ser. No. 17/124,361, filed Dec. 16, 2020, which claims priority to U.S. Provisional Application No. 62/948,591, filed Dec. 16, 2019, the disclosure of each of which is incorporated herein by reference.

FIELD OF THE INVENTION

The present invention relates to a new process for the production of an arginine-silicate complex.

BACKGROUND OF THE INVENTION

Methods of producing arginine-silicate complexes (ASI) are taught in U.S. Pat. No. 6,803,456, which is incorporated herein in its entirety. The dietary supplement NITROSIGINE is a patented source of inositol-stabilized arginine silicate (ASI). Pre-clinical studies of ASI demonstrated superiority of this dietary ingredient over arginine in blood flow markers and have been shown to positively affect silicon absorption. The dietary supplement provides evidence of health benefits.

One problem with the current manufacturing and use of bulk ASI powder is that the ASI can clump. Some of the production lots tend to clump more quickly than other lots and to different degrees. Particle samples of various lots were evaluated during the manufacturing process. The results revealed that particles were present in various shapes and circumferences, with some degree of fractured or partial particles. There was no uniformity of shape and circumference. Because there is a lack of consistency in the particles and powder make up, and because there are clumping and solubility issues, there is a need for new and/or improved methods of manufacture to reduce and/or eliminate the clumping issue and to increase the solubility of the final product. The present invention provides methods for manufacturing that produces a particle size distribution to reduce and/or eliminate the clumping issue and increases the solubility of the ASI complex.

SUMMARY OF THE INVENTION

The present invention provides methods of producing ASI products and ASI complexes with reduced clumping or absence of clumping and increased solubility as compared to known methods. In certain embodiments, the methods reduce or eliminate clumping by producing specific particle or sphere size distributions. In other embodiments, an ASI product or ASI complex is provided with reduced clumping or no clumping, and increased solubility. In certain embodiments, an ASI complex is provided for inclusion in liquids, wherein the ASI complex has reduced or eliminated clumping characteristics, and increased solubility. Some embodiments provide nutritional and/or food beverages with ASI complexes with reduced or eliminated clumping characteristics, and increased solubility. In yet another embodiment, the methods reduce or eliminate clumping, increasing solubility by producing multiple particle size distribution more sphere sizes and particle shapes. In certain other embodiments, the present invention provides methods of reducing or eliminating clumping by producing particle spheres with reduced amounts of broken spheres or with the elimination of broken spheres.

DETAILED DESCRIPTION OF THE INVENTION

Figure 1:
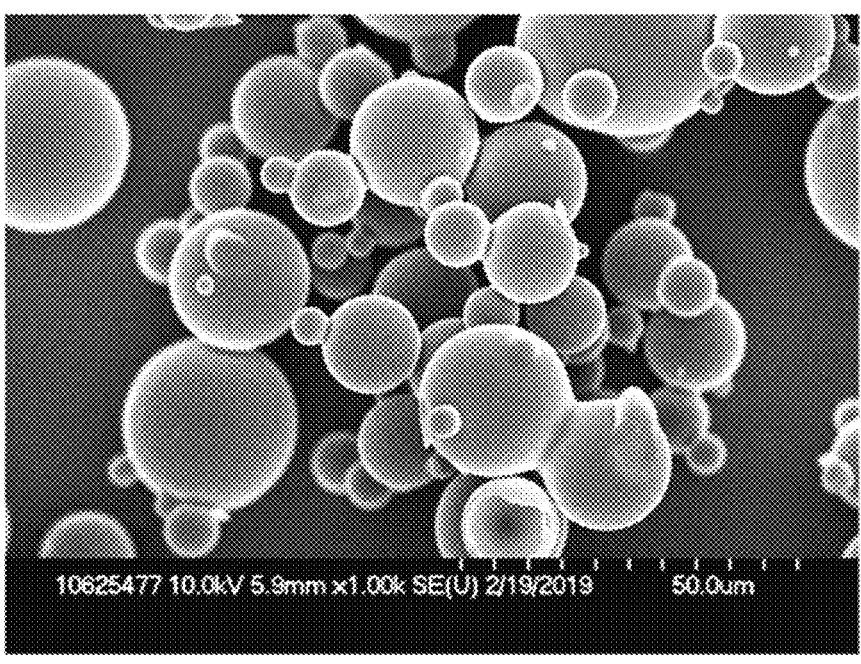
FIG. 1 is a low magnification (Micron Bar=10×5 μm=50 μm) image illustrating typical structures present in a sample batch of a known ASI product.

The present invention is a process of making inositol-stabilized arginine-silicate complexes. Known methods of producing ASI are found in U.S. Pat. No. 6,803,456, which is incorporated herein in its entirety. The present invention provides steps to improve those methods by modifying the process to reduce unwanted clumping of the resulting ASI product.

As described in the patented process in U.S. Pat. No. 6,803,456, arginine is combined with a silicate salt and inositol at elevated temperature to form a suspension or solution, which, if not in solution, is heated to result in solution. The initial mixing temperature is preferably at least about 30° C., more preferably at least about 40° C., still more preferably at least about 50° C., even more preferably at least about 60° C. The initial mixing temperature can be chosen to balance energy costs and safety (keeping the temperature as low as possible) and speed of dissolution (raising the temperature as high as practical). Whether or not the initial mixture is a suspension or solution and regardless of the initial mixing temperature, the mixture is to be heated to about at least 80° C., preferably to about at least 90° C., more preferably to about 95° C. to assure proper formation of the desired complex solution prior to the spray drying step. Preferably, once raised to the at least 80° C. temperature, the material (solution/suspension) should be maintained at this temperature for at least about 4 minutes, more preferably for at least about 4.5 minutes, still more preferably at least about 5 minutes. The solution temperature can then be reduced as long as gel formation and crystallization do not take place, and the complex is maintained in solution. Generally, the temperature should not be reduced below about 55° C. in order to maintain the complex in solution before it is spray dried. However, if the solution is allowed to cool below this temperature and the product begins to show some precipitation, heating to above about 55° C. before spray drying usually brings the precipitate back into solution so that the solution can then be spray dried. In general, the spray drying can take place close to the time of dissolution and raising the temperature to the at least 80° C. temperature, so that little or no appreciable cooling takes place.

Once the arginine-silicate-inositol complex has been formed and is in solution, the solution is introduced into a spray drier. Any spray drying apparatus may be used, but a conical or flat bottom spray drier is preferred.

Because the primary use of the product is for a pharmaceutical or nutritional supplement purpose, pharmaceutically acceptable silicate salts are preferred. Preferably, the silicate salt is potassium silicate, although any other silicate salt that is acceptable for the end use is also suitable. Sodium silicate and magnesium silicate are particularly suitable alternatives, although other suitable silicates will be apparent to those of ordinary skill in this field. Preferably, the silicate has a low iron and/or low copper content so that the final arginine-silicate-polyol complex has a copper content of preferably 0 to not greater than about 50 ppm, more preferably 0 to not greater than about 40 ppm, still more preferably 0 to about 30 ppm, even more preferably 0 to not greater than about 20 ppm, most preferably 0 to not greater than about 10 ppm; and/or an iron content of preferably 0 to not greater than about 100 ppm, more preferably 0 to not greater than about 75 ppm, still more preferably 0 to about 50 ppm, even more preferably 0 to about 40 ppm, most preferably 0 to not greater than about 10 ppm. In addition, preferably the total heavy metal content of the complex should be 0 to not greater than about 20 ppm in order meet the current FDA maximum heavy metal content requirements. Generally commercially available electronic grade silicate material will meet the iron, copper, and heavy metal content requirements above. Furthermore, where the silicate is not a sodium silicate, the sodium content of the final arginine-silicate-polyol complex is preferably 0 to not greater than about 500 ppm, more preferably 0 to not greater than about 400 ppm, even more preferably 0 to not greater than about 350 ppm, most preferably 0 to not greater than about 320 ppm.

The complexes prepared in U.S. Pat. No. 6,803,456 employ inositol. Inositol is the most preferred material for the complex so that the most preferred complex for the invention is the arginine-silicate-inositol. For the remainder of this disclosure, reference to the "complex" without qualification means arginine-silicate-inositol complex, unless the context dictates otherwise.

In general, the molar ratio of arginine to silicate is about 0.5:1 to about 2:1, preferably about 0.75:1 to about 1.25:1, more preferably about 0.8:1 to about 1.2:1. Particularly suitable ratios of arginine:silicate include, among others, 1:1, 0.97:1, and 0.933:1. These ratios can be adjusted in the methods disclosed herein to reduce or eliminate the clumping and increase solubility of the produced ASI.

The molar ratio of the arginine to polyol (e.g., inositol) is typically in the range of about 1:1 to about 4:1, preferably about 1.25:1 to about 3:1, more preferably about 1.5:1 to about 3:1. Particularly suitable ratios include, without limitation about 3.25:about 1; about 3:about 1; about 2:about 1; about 1.75:about 1; and about 1.5:about 1. These ratios can be adjusted in the methods disclosed herein to reduce or eliminate unwanted clumping and increase solubility of the produced ASI.

The mixture resulting from the combination of inositol, silicate salt and arginine is a highly viscous suspension/solution, which is clarified by heating. In a preferred embodiment, the suspension/solution is heated to between about 80° C. and about 100° C., more preferably about 95° C., until clarification is observed. These temperatures can be increased or decreased as necessary in the methods disclosed herein to reduce or eliminate the unwanted clumping and increase solubility of the produced ASI.

Generally this requires at least about 4.5 minutes, preferably at least about 5 minutes of maintaining the temperature above the "between about 80° C. and about 100° C." range. At this time, heating and stirring is discontinued. The solution is then introduced into a spray drier to obtain suitable product. The time for heating and stirring may be adjusted, as determined, to avoid the unwanted clumping of the resulting ASI. Further, the methods of the present invention provides for adjustments to temperatures, and to rotary and nozzle atomization to obtain the desired size and concentrations/percentages of particle sizes.

While it is believed that crystallization and gel formation are to be avoided, this can be determined as it relates to low solubility and the unwanted clumping does not occur. In those instances where immediate introduction into a spray drier is not possible, the clarified solution should be maintained at a sufficiently high temperature so as to avoid gel formation and crystallization. However, if some crystallization does occur, reheating to at least about 55° C. should re-dissolve the crystals and the product may then be introduced into the spray drier. As can be determined, any reheating steps addressing crystallization may be eliminated to avoid potential issues with broken or misshapen particles of ASI (e.g., spheres) that might lead to clumping.

Other means of dispensing the resulting ASI can be employed as necessary to avoid the unwanted clumping of the resulting ASI particles (e.g., spheres). Also, those means of dispensing the resulting ASI can include such means that permit desired particle size distributions, a more preferred particle shape, less broken particles (e.g., broken spheres), and/or combination thereof. This can involve inter alia using varied conical diameters for the spray drying steps, or such methods utilized in micronization to better control particle sizes to be within a preferred range of average diameter/sizes of the particles, which might reduce or eliminate the unwanted clumping and increase solubility of the ASI.

When addressing ASI particles, the different particle morphologies can be addressed and tested to determine the best ratios of the differing aspects of particle morphologies. Particle morphology can be described in terms of particle size, shape, internal structure, densities, and surface properties. As used herein, the different morphologies to be addressed and tested for reducing or eliminating unwanted clumping are discussed as relevant to that particular section of this disclosure.

To reduce or eliminate unwanted clumping and increase solubility, the method steps provided herein are modified to produce desired particle (e.g., sphere) sizes and particle size distributions. As a result of the modifications, particle sizes can be within an average size range of 1 to 50 μm of each other; preferably within 1 to 40 μm; more preferably 1 to 30 μm; even more preferably 1 to 20 μm; and most preferably 1 to 10 μm or 1 to 5 μm of each other.

In another method of the present invention, manufacturing steps can be performed and modified as necessary to achieve a preferred mixture of ASI particle shapes (e.g., spheres) to reduce or eliminate the unwanted clumping and increase solubility. The impact of different morphologies on unwanted clumping and solubility can be determined. That data can then be used to modify the method steps as necessary to produce varying ranges of morphologies relating to the level of one shape compared to other shapes. As necessary, the ratios of the various morphologies can be adjusted to produce the best desired ratio to reduce or eliminate the unwanted clumping and to increase the solubility. Such modifications or additional steps might involve tuning colloidal interactions in the suspensions. From these steps, a model can be developed to relate colloidal interaction potential to critical pressure exerted by solvent(s) in the flow. This can allow a more predictive particle shape.

In another method of the present invention, the impact of the presence and levels of incomplete particles will be determined. As used herein, incomplete particles includes, without limitations, incomplete complexes, broken particles, shattered or broken spheres, and combinations thereof. With the determination of the impacts of the incomplete particles on the clumping effect, modifications or additional steps will be taken to reduce or eliminate the impact on the clumping and increase solubility in the final product.

As shown herein, known methods of ASI production can lead to unwanted clumping and lowered solubility in the final product. Shown in FIGS. 1-10 are some examples of the unwanted clumping and other characteristics of a known ASI product. Each example used product samples that were sprinkled on an adhesive carbon tab attached to an SEM stub. Excess material was removed using a blast of air prior to gold and platinum/palladium coating.

Figure 2:
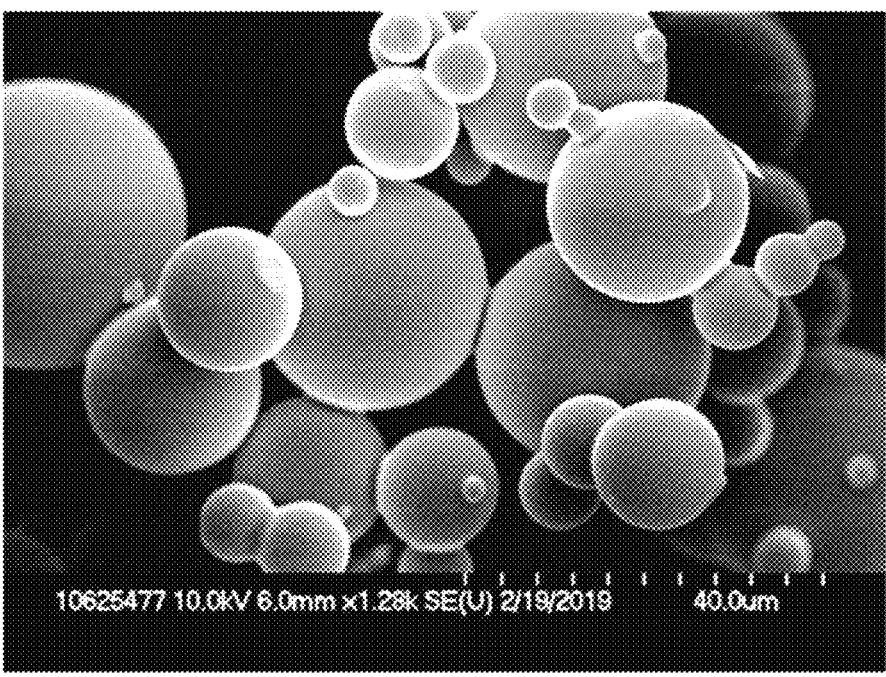
FIG. 2 is a higher magnification (Micron Bar=10×4 μm=40 μm) image illustrating how the particles of a known ASI product aggregate together.
Figure 3:
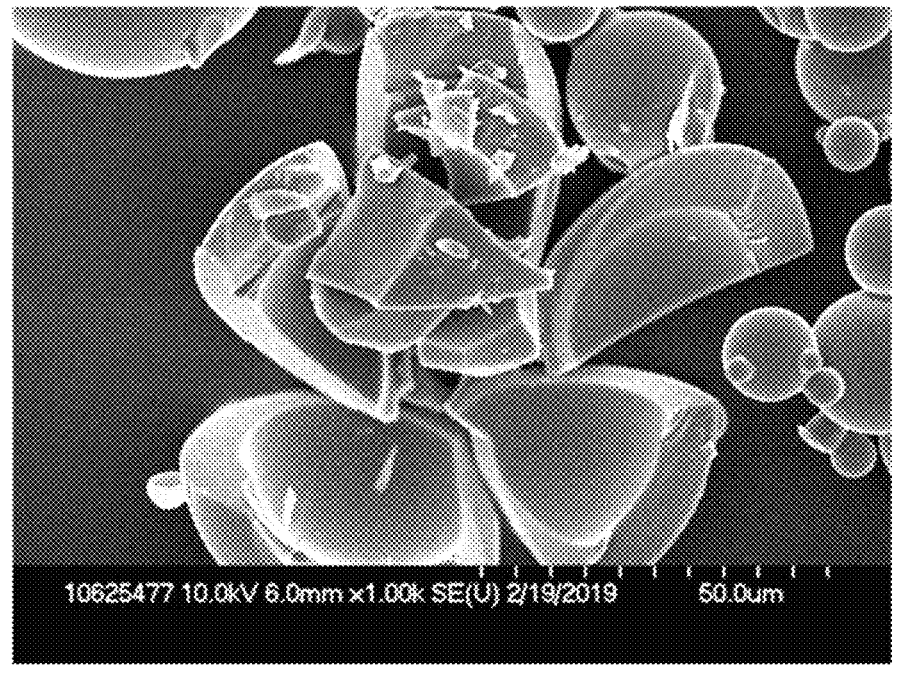
FIG. 3 is an image (Micron Bar=10×5.0 μm=50 μm) illustrating how particles of a known ASI product have broken apart, resulting in several pieces, and wherein the particle had a hollow interior.
Figure 4:
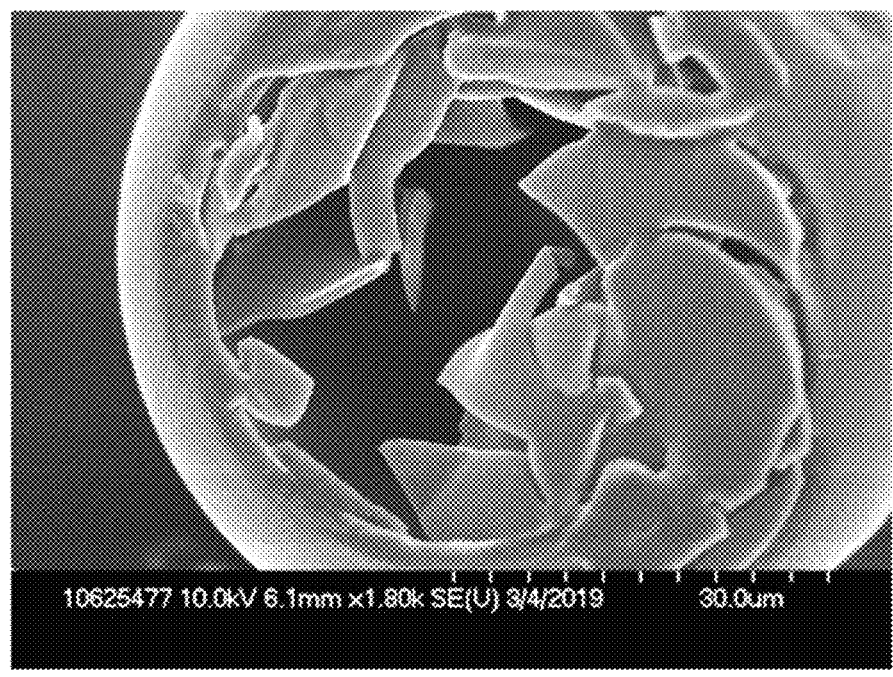
FIG. 4 is an image (Micron Bar=10×3 μm=30 μm) illustrating a particle of a known ASI product breaking into smaller fragments, which shows the hollow interior.
Figure 5:
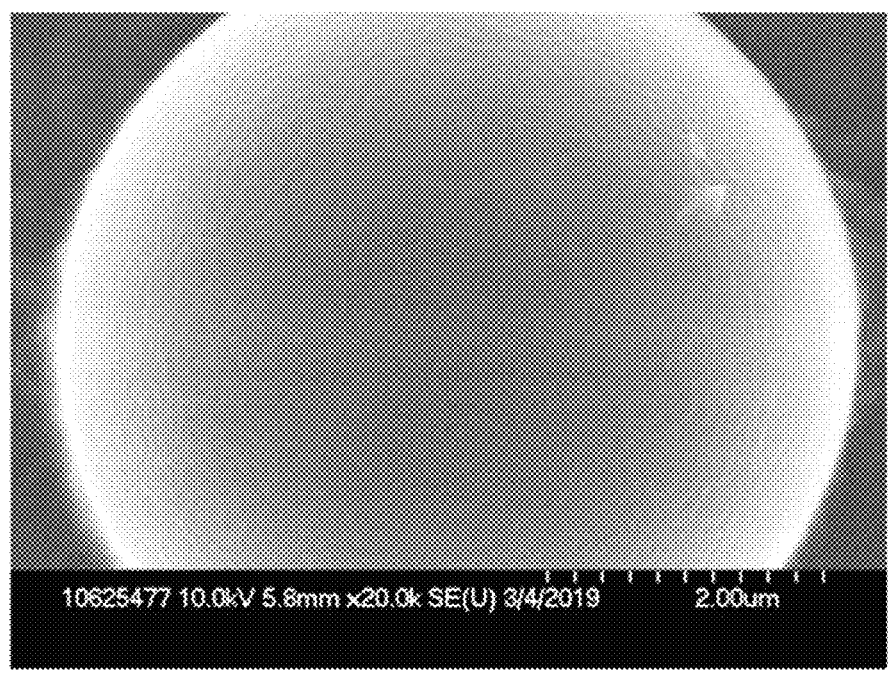
FIG. 5 provides a high magnification image (Micron Bar=10×200 nm=2 μm) illustrating one of the typical, intact structures found in a sample batch.
Figure 6:
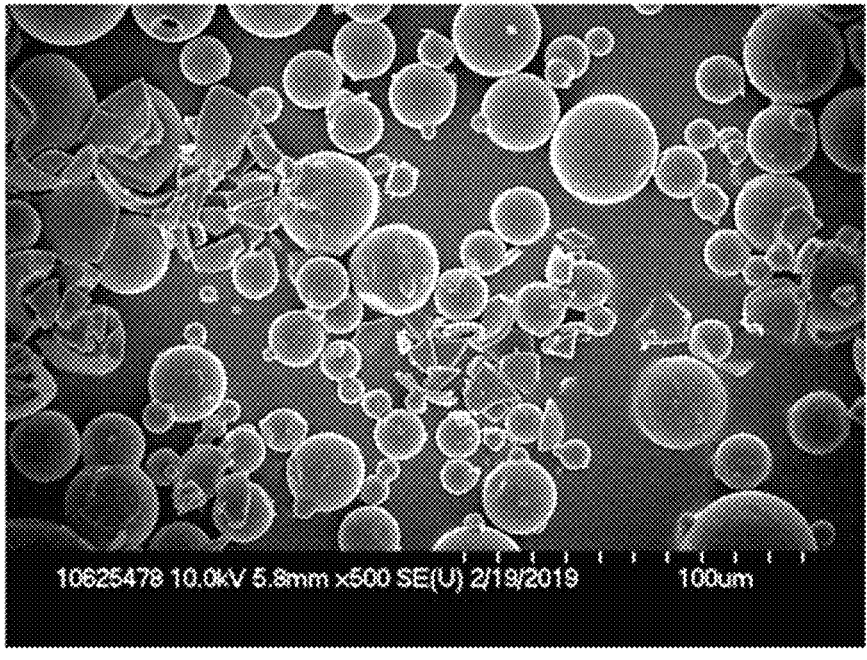
FIG. 6 provides an image (Micron Bar=10×10 μm=100 μm) illustrating assorted structures typical within a sample batch.
Figure 7:
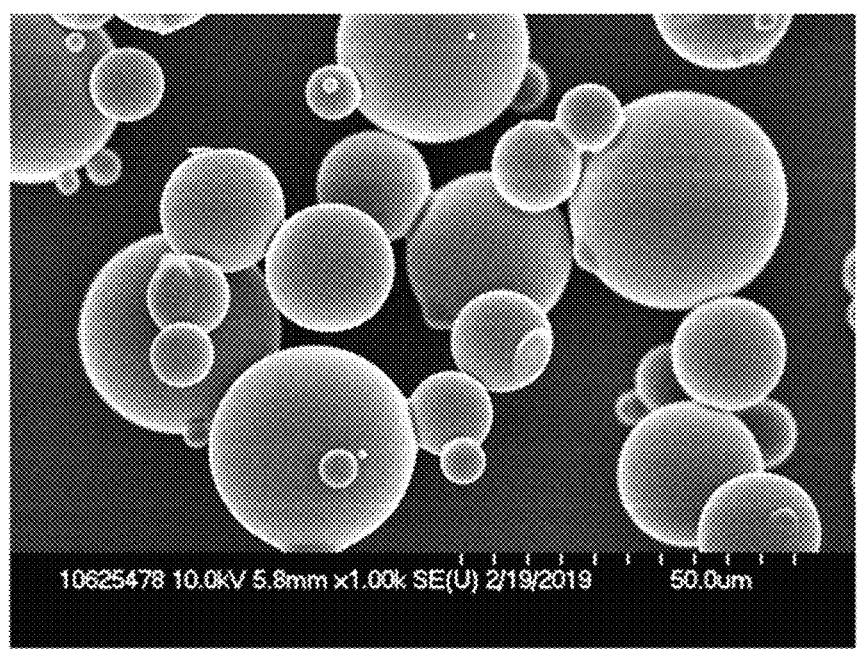
FIG. 7 provides an image (Micron Bar=10×5.0 μm=50 μm) illustrating variation in structural size and presence of aggregation.
Figure 8:
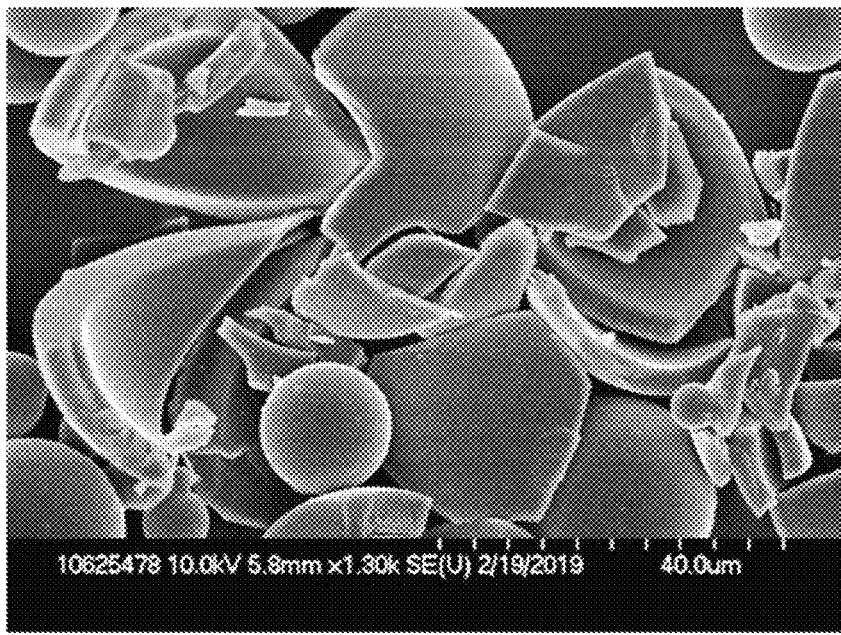
FIG. 8 provides an image (Micron Bar=10×4 μm=40 μm) illustrating particles that broke apart into multiple pieces, and showing hollow interiors.
Figure 9:
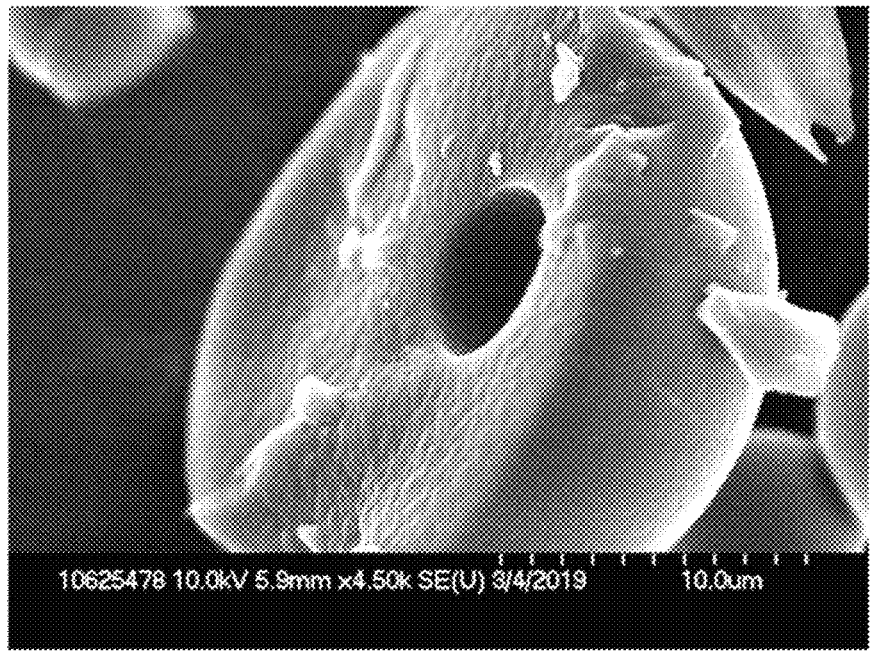
FIG. 9 provides an image (Micron Bar=10×1 μm=10 μm) illustrating a particle split in two, with a thicker inner layer and a hollow center.
Figure 10:
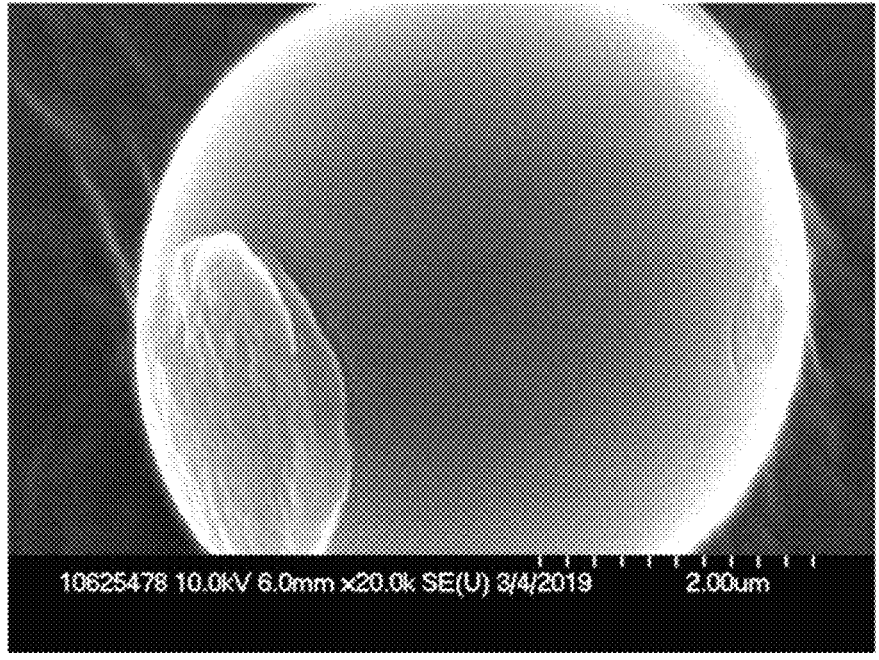
FIG. 10 provides an image (Micron Bar=10×200 nm=2 μm) illustrating variation in the manufactured/processed structural size of a sample batch.

FIG. 1 illustrates typical structures present in the known sample batch. FIG. 2 illustrates how the particles aggregate together. FIGS. 3-4 and 7-9 illustrate how broken and fragmented particles with hollow interiors. FIGS. 5-6 provide aspects of typical, intact structures found in a sample batch. FIG. 10 illustrates the variation in the manufactured/processed structural size of a sample batch of a known ASI product.

To avoid unwanted variations that can lead to increased clumping and lowered solubility, the methods of making inositol-stabilized arginine-silicate complexes of the present invention utilizes steps that alter and/or guide formation of the ASI complexes in a way that appropriately addresses the sphere shape differences, particle size differences, shattering or breaking up of particles, particle densities related to the interior space or structure, or combinations thereof.

In the manufacture of the product resulting from the methods provided herein, steps are performed to provide a particle size distribution, which results in a combination of increased solubility and reduced clumping.

During various attempts to solve known obstacles to overcoming ASI clumping and lowered solubility, a product with very small particles was made; however, the product clumped very quickly when exposed to air. Thus, production of an ASI product comprising a fine powder did not overcome the clumping or low solubility issues with the products from known methods. Similarly, when a product of larger, coarser particles was made and tested, it was found that these coarser particle products suffered the same clumping and low solubility issues.

Figure 11:
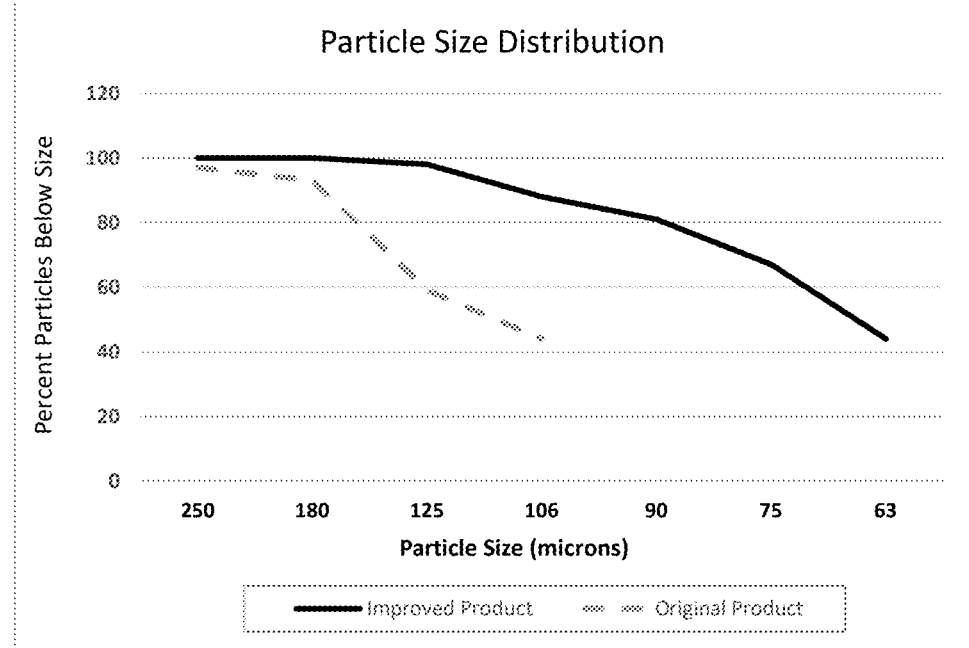
FIG. 11 is a chart illustrating a particle size distribution of an ASI product of the invention compared to a known ASI product.

Based on these issues, method steps were taken to produce particle size distributions that reduced clumping and enhanced solubility over the known products. The present invention provides for sphere size range(s) or particle size distributions that significantly improve solubility and reduce clumping. FIG. 11 is a graph demonstrating the distribution of particle sizes of a known ASI complex product (dashed line) compared to a product of the instant invention (solid line).

The following table is a further comparison of the known ASI product to that of a product of the instant invention. This table provides a side-by-side comparison of the importance of selecting an adequate particle size distribution. It was unexpected that, as seen in the above-chart and the table below, the products of the instant invention would result in improved solubility and reduced or eliminated clumping characteristics. Specifically, products within the particle size distributions of the instant invention resulted in clearer appearance when added to water; and there was no clumping or there was significantly reduced clumping.

| | Percent Below Size | |
|---|---|---|
| Size (uM) | Improved Product | Original Product |
| 250 | 100 | 97 |
| 180 | 100 | 93 |
| 125 | 98 | 59 |
| 106 | 88 | 44 |
| 90 | 81 | |
| 75 | 67 | |
| 63 | 44 | |

As discussed herein, it was believed that reducing the average particle size so that all particles were a fine powder, e.g., 100% of particles were less than 74 μm; however, this approach resulted in near immediate clumping upon exposure to air, despite having a slight improvement in solubility. Attempts to approach a solution to the problems through increasing the average particle size above a certain level resulted in heavy clumping and sinking without dissolution. For these reasons, methods were developed to approach the ASI solubility and clumping problems from both directions.

As seen in the above table and in FIG. 11, superior results in reducing clumping and increasing solubility were achieved through an unexpected mixture of particle size distributions. These product characteristics are shown in the above table and in FIG. 11, wherein the particle size distribution of a product of this invention is compared to the particle distribution of the product of methods known in the art.

A preferred particle size distribution of the ASI composition of the present invention includes a mixture of particles comprising approximately 67% of particles with sizes between about 0.1 μm and about 75 μm, and approximately 33% of particles sizes between about 76 μm and about 200 μm. In another particle size distribution, the ASI composition comprises at least 50% of particles with sizes between about 0.1 μm and about 75 μm, and approximately 50% between about 76 μm and about 200 μm. While these are some of the preferred embodiments of products from the methods provided herein, it was found that differing levels of reduced clumping and increased solubility is achievable through the data presented in the chart and table provided herein. In one aspect, 98% of the particles of a product of the invention passed through a 125 micron mesh size, meaning that 98% of the particles were of both size and shape to pass through the mesh, as opposed to only 59% of the known ASI product.

These unexpected and surprising results address the clumping and low solubility issues associated with the known ASI products and the methods of producing the same. With these problems addressed, the ASI complexes of the methods of the instant invention have a better shipping and storing stability by avoiding the clumping issues known to occur. As with the clumping reduced or eliminated, solubility of the ASI complexes is also addressed. With the increased solubility, the ASI products are more operable and preferable for use in nutritional beverages, dietary supplement beverages and other liquid forms to be used in the market place. Thus, the unexpected reduction in clumping and the increased solubility changes the operability of ASI complexes in the market place over the known ASI-related products.

As will be appreciated, the methods, and the modifications and additions to the methods discussed herein, are to improve the manufactured ASI product. As will also be appreciated, the methods disclosed herein may be performed in whole or in part to address different morphology issues related to the particles that impact the unwanted clumping of the manufactured ASI product. It is expected that there will be modifications and additions that are within the spirit of the present disclosure.

What is claimed is:

1. An inositol-stabilized arginine-silicate ("ASI") complex comprising a plurality of ASI particles, wherein the plurality of ASI particles has a particle size distribution wherein from 2% to 12% of the particles are of a size of at least 125 μm.

2. The ASI complex of claim 1, wherein less than 3% of the particles are of a size of at least 250 μm.

3. The ASI complex of claim 1, wherein less than 7% of the particles are of a size of at least 180 μm.

4. The ASI complex of claim 1, wherein from 12% to 19% of the particles are of a size of at least 90 μm.

5. The ASI complex of claim 1, wherein from 88% to 98% of the particles are of a size less than 106 μm.

6. The ASI complex of claim 1, wherein from 81% to 88% of the particles are of a size less than 90 μm.

7. The ASI complex of claim 1, wherein from 67% to 81% of the particles are of a size less than 75 μm.

8. The ASI complex of claim 1, wherein from 44% to 67% of the particles are of a size less than 63 μm.

9. An inositol-stabilized arginine-silicate ("ASI") complex comprising a plurality of ASI particles, wherein the plurality of ASI particles has a particle size distribution wherein from 2% to 12% of the particles are of a size of at least 106 μm.

10. The ASI complex of claim 9, wherein less than 3% of the particles are of a size of at least 250 μm.

11. An inositol-stabilized arginine-silicate ("ASI") complex comprising a plurality of ASI particles, wherein the plurality of ASI particles has a particle size distribution wherein less than 56% of the particles are of a size of from 63 μm to 250 μm, and at least 2% of the particles are of a size of from 125 μm to 250 μm.

12. The ASI complex of claim 11, wherein less than 56% of the particles are of a size of from 63 μm to 180 μm.

13. The ASI complex of claim 11, wherein less than 54% of the particles are of a size of from 63 μm to 125 μm.

14. The ASI complex of claim 11, wherein less than 33% of the particles are of a size of from 75 μm to 180 μm.

15. The ASI complex of claim 11, wherein less than 31% of the particles are of a size of from 75 μm to 125 μm.

16. The ASI complex of claim 11, wherein less than 10% of particles are of a size between 106 μm and 125 μm.

17. The ASI complex of claim 11, wherein less than 21% of the particles are of a size between 75 μm and 125 μm.

18. The ASI complex of claim 11, wherein less than 17% of the particles are of a size of from 90 μm to 125 μm.

19. The ASI complex of claim 11, wherein at least 2% of the particles are of a size of from 125 μm to 180 μm.

20. The ASI complex of claim 11, wherein less than 1% of the particles are of a size of from 180 μm to 250 μm.

* * * * *